United States Patent [19]

Jacobsen et al.

[11] Patent Number: 4,584,868

[45] Date of Patent: Apr. 29, 1986

[54] APPARATUS FOR DETERMINING THE SUPERCOMPRESSIBILITY FACTOR OF A FLOWING GAS

[75] Inventors: Robert S. Jacobsen, Hatboro; George W. Schneider, Jr., Huntingdon Valley, both of Pa.

[73] Assignee: American Meter Company, Philadelphia, Pa.

[21] Appl. No.: 734,935

[22] Filed: May 16, 1985

[51] Int. Cl.$^4$ .......................... G01N 7/00; G01F 1/00
[52] U.S. Cl. ...................................... 73/23; 73/861.03
[58] Field of Search .................. 73/23, 861.02, 861.03; 364/510

[56] References Cited

U.S. PATENT DOCUMENTS 3,701,280 10/1972 Stroman .................................. 73/23
4,390,956 6/1983 Cornforth et al. ............... 73/861.03

Primary Examiner—Stephen A. Kreitman
Attorney, Agent, or Firm—David L. Davis; Robert E. Smith; Edward L. Bell

[57] ABSTRACT

An arrangement for determining the supercompressibility factor of a flowing gas at elevated pressure includes a first meter for measuring the volume flow rate of the gas at the elevated pressure, a restrictor at the outlet of the first meter for dropping the pressure of the gas to a pressure at which the supercompressibility factor is known, and a second meter for measuring the volume flow rate of the gas at the lower pressure. A computer calculates the supercompressibility factor of the gas at the elevated pressure by utilizing measured values of temperature, pressure and volume flow rate of the gas at both the elevated and lower pressures.

4 Claims, 1 Drawing Figure

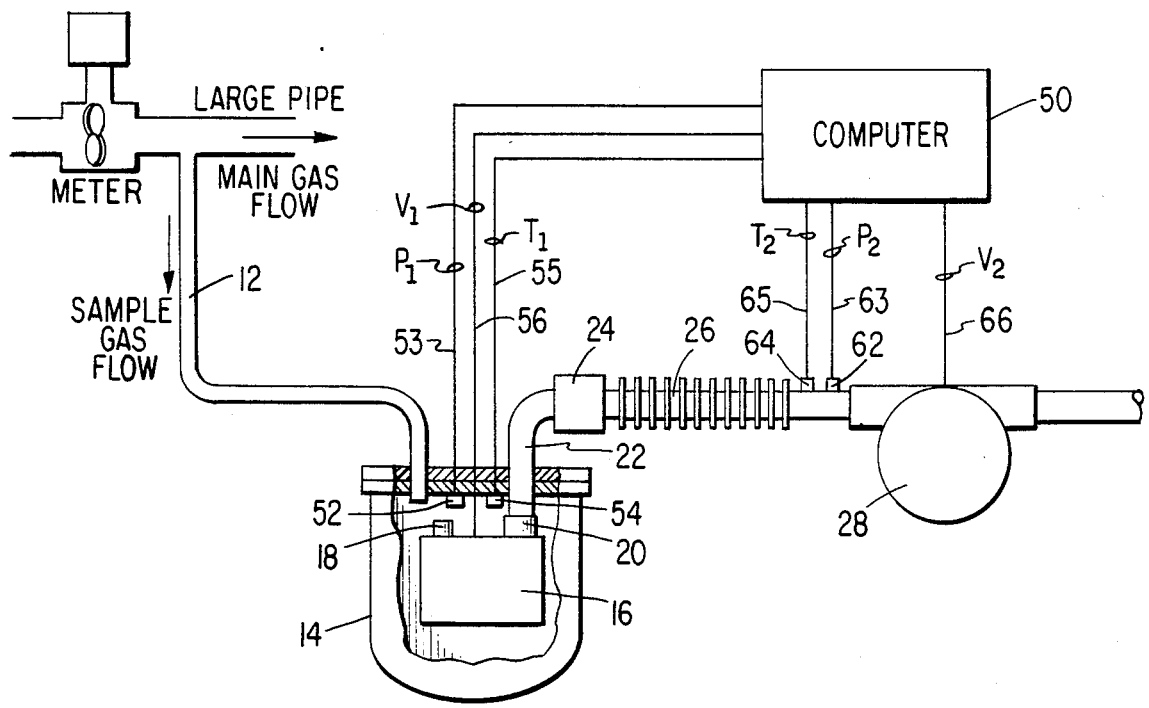

APPARATUS FOR DETERMINING THE SUPERCOMPRESSIBILITY FACTOR OF A FLOWING GAS

DESCRIPTION

BACKGROUND OF THE INVENTION

This invention relates to gas flow measurement and, more particularly, to the determination of the supercompressibility factor of a flowing gas subject to volume measurement.

The rapidly increasing cost of natural gas since the 1970's has caused profound changes in attitudes towards meter accuracy, especially when gas at high pressure is involved. Thus, increasing attention has been focused upon providing an accurate measure of the volume of gas flowing through a pipeline. However, all volumetric meters measure actual volume and, since gas is a compressible item, the volume of which changes as a function of temperature and pressure, calculations must be made to convert the measured gas flow volume to a standard volume at a specified, previously agreed upon, base condition of temperature and pressure.

U.S. Pat. No. 4,390,956, discloses an apparatus for performing the correction calculations. In that disclosed apparatus, the major part of the calculations are involved with determining the supercompressibility factor of the flowing gas, based upon measured temperature and pressure and a set of constants entered into the apparatus for a particular gas composition. Thus, if the gas composition changes, a new set of constants must be entered into the apparatus.

It is therefore an object of the present invention to provide an arrangement for determining the supercompressibility factor of a flowing gas.

It is a further object of this invention to provide such an arrangement which is automatically adaptive to changing gas compositions.

SUMMARY OF THE INVENTION

The foregoing and other objects of this invention are attained in accordance with the principles of this invention by providing an arrangement for continuously determining the supercompressibility factor ($Z_1$) of a gas at an elevated pressure ($P_1$), comprising means for dropping the pressure of the gas to a lower pressure ($P_2$) at which the supercompressibility factor ($Z_2$) of the gas is known, means for measuring the volume ($V_1$), temperature ($T_1$) and pressure ($P_1$) of the gas at the elevated pressure, means for measuring the volume ($V_2$), temperature ($T_2$), and pressure ($P_2$) of the gas at the lower pressure, and means for calculating the elevated pressure supercompressibility factor using the formula $$Z_1 = \frac{V_1}{V_2} \times \frac{P_1}{P_2} \times \frac{T_2}{T_1} \times Z_2.$$

BRIEF DESCRIPTION OF THE DRAWING

The foregoing will be more readily apparent upon reading the following description in conjunction with the single figure of the drawing which is a schematic illustration of apparatus constructed in accordance with the principles of the invention.

DETAILED DESCRIPTION

Until the present time, there have been three common methods to determine the supercompressibility factor of a gas. The first method, developed during the 1930's, is to make a measurement using an apparatus known as the Bean-Burnett apparatus or some other similar apparatus. The second method is to analyze the gas, finding all its components, and then use an equation of state to perform a theoretical calculation to determine the supercompressibility factor. The third method is the one that is most commonly used throughout the gas industry and this is to utilize the tables or formulas set forth in the "Manual for the Determination of Supercompressibility Factors for Natural Gas", PAR Research Projects NX-19, published by the American Gas Association. These three methods do not result in the same answer for the same gas—the results are close, but none of them are 100% accurate. Thus, when performing a theoretical calculation, the result depends on what equation of state is utilized. Another disadvantage is that when using a gas analyzer, such as a gas chromatograph, this takes a certain amount of time to run and there are a number of maintenance procedures that are necessary.

In accordance with the present invention, use is made of Boyle's and Charles' laws which state that, for a given gas at two conditions of pressure and temperature:

$$\frac{V_1 P_1}{T_1 Z_1} = \frac{V_2 P_2}{T_2 Z_2}$$

where:
$P_1$ is the pressure of the first condition;
$V_1$ is the volume at the first condition;
$T_1$ is the temperature at the first condition;
$Z_1$ is the supercompressibility factor at the first condition;
$P_2$ is the pressure at the second condition;
$V_2$ is the volume at the second condition;
$T_2$ is the temperature at the second condition;
$Z_2$ is the supercompressibility factor at the second condition.

Accordingly, the supercompressibility factor at the first condition can be expressed as $$Z_1 = \frac{V_1}{V_2} \times \frac{P_1}{P_2} \times \frac{T_2}{T_1} \times Z_2.$$

Thus, if the volume, pressure and temperature can be measured at the two conditions and if the supercompressibility factor $Z_2$ at the second condition is known, then it is a simple matter to calculate the unknown supercompressibility factor $Z_1$.

In actual practice, the determination of the supercompressibility factor only comes into play with respect to high pressure gas flow. This would be under the conditions denoted by the subscript 1 in the above equations. The conditions denoted by the subscript 2 in the equations above would have to be some conditions at which the supercompressibility factor of the flowing gas were known, the other variables being susceptible to direct measurement. Since for natural gas at atmospheric pressure and 60° F. temperature the supercompressibility factor is almost exactly equal to unity, if the high pressure gas can be expanded to atmosphere and the conditions under high pressure and at atmosphere can be measured, the high pressure supercompressibility factor can then be determined. The single figure schematically illustrates an arrangement for determining the supercompressibility factor in accordance with this invention.

Thus, some of the high pressure gas in the system is taken from the main pipeline to the apparatus according to this invention by means of a smaller pipe 12, illustratively one quarter inch diameter. In a typical application, the gas in the pipe 12 is at meter pressure on the order of fifty atmospheres. Since only a relatively small volume of gas is taken by the pipe 12, only a small capacity meter is required to measure the volume of the test sample. However, small capacity meters are generally not able to withstand high pressure so the pipe 12 is fed into a pressure vessel 14, within which there is disposed a meter 16. The meter 16 may be an aluminum case diaphragm meter but since the pressures on the outside and the inside of the meter are equal, the meter 16 being within the pressure vessel 14, this type of meter is entirely satisfactory for the purposes described herein. The inlet 18 of the meter 16 is open to the interior of the pressure vessel 14 and the outlet 20 of the meter 16 exits the pressure vessel 14 through a pipe 22. The gas in the pipe 22 is still at the high pressure. In order to drop the pressure of the gas, a restrictor 24 is provided. The output of the restrictor 24 is connected to a heat exchanger 26 which in turn is connected to the input of a meter 28, the output of which is vented at near atmospheric pressure. The restrictor 24 may be any type of orifice, including an orifice plate or a sonic nozzle. When the pressure of the gas is dropped across the restrictor 24 from about fifty atmospheres to one atmosphere, its volume increases and its temperature decreases. The heat exchanger 26 is for the purpose of raising the temperature of the expanded gas to ambient, which is the temperature of the meter 28. The meter 28 must be a high capacity meter, such as a rotary meter, because the volume passing through the meter 28 at the reduced pressure will be on the order of fifty times the volume of the gas passing through the meter 16 at the elevated pressure.

To make the necessary calculations, there is provided a computer 50. To provide the computer 50 with actual values to perform the calculations, there are provided within the pressure vessel 14 a pressure sensor 52 and a temperature sensor 54, coupled to the computer 50 via the lines 53 and 55, respectively. The computer is also provided with volume pulses from the meter 16 over the line 56. Thus, the lines 53, 55 and 56 carry signals representative of the quantities $P_1$, $T_1$ and $V_1$, respectively. Similarly, at the input to the meter 28 there is provided a pressure sensor 62 and a temperature sensor 64, connected to the computer 50 via the leads 63 and 65, respectively. Also, volume pulses from the meter 28 are provided to the computer 50 via the lead 66. Thus, the leads 63, 65 and 66 carry signals representative of the quantities $P_2$, $T_2$, and $V_2$, respectively. The computer 50 then calculates the supercompressibility factor ($Z_1$) of the high pressure input gas by using the formula $$Z_1 = \frac{V_1}{V_2} \times \frac{P_1}{P_2} \times \frac{T_2}{T_1} \times Z_2.$$

Since the gas at the second condition is at atmosphere and ambient temperature, the supercompressibility factor $Z_2$ of this gas is sufficiently close to unity that $Z_2$ can be taken to be equal to one and can be dropped from the above equation, or a small correction typically $<0.2\%$ can be made.

The results of this calculation can be used to correct the measured volume of the high pressure flowing gas, such as by transmitting the calculated supercompressibility factor to an apparatus such as that described in the aforementioned patent. A particular advantage of the presently disclosed arrangement is that the supercompressibility factor is obtained in a real time basis with relatively inexpensive equipment, since no gas analysis equipment is necessary.

Accordingly, there has been disclosed an arrangement for determining the supercompressibility factor of a gas at an elevated pressure. It is understood that the above-described embodiment is merely illustrative of the application of the principles of this invention. Numerous other arrangements may be devised by those skilled in the art without departing from the spirit and scope of this invention, as defined by the appended claims.

We claim:

1. An arrangement for continuously determining the supercompressibility factor ($Z_1$) of a gas at an elevated pressure ($P_1$), comprising:
    means for dropping the pressure of said gas to a lower pressure ($P_2$) at which the supercompressibility factor ($Z_2$) of said gas is known;
    means for measuring the volume ($V_1$) of said gas at said elevated pressure;
    means for measuring the temperature ($T_1$) of said gas at said elevated pressure;
    means for measuring said elevated pressure ($P_1$);
    means for measuring the volume ($V_2$) of said gas at said lower pressure;
    means for measuring the temperature ($T_2$) of said gas at said lower pressure;
    means for measuring said lower pressure ($P_2$); and
    means for calculating said elevated pressure supercompressibility factor using the formula $$Z_1 = \frac{V_1}{V_2} \times \frac{P_1}{P_2} \times \frac{T_2}{T_1} \times Z_2.$$

2. The arrangement according to claim 1 wherein said pressure dropping means comprises a restrictor.

3. The arrangement according to claim 1 further including means for raising the temperature of said lower pressure gas to ambient temperature.

4. The arrangement according to claim 3 wherein said temperature raising means includes a finned heat exchanger.

* * * * *